(12) United States Patent
Calderwood et al.

(10) Patent No.: US 7,661,880 B2
(45) Date of Patent: Feb. 16, 2010

(54) RADIOGRAPHIC SENSOR POSITIONING SYSTEM

(76) Inventors: Mitchell C. Calderwood, 340 S. Kellogg, Suite G, Goleta, CA (US) 93117; William B. Schmitz, 1001 E. Morton Pl., Suite B, Hemet, CA (US) 92543

( * ) Notice: Subject to any disclaimer, the term of this patent is extended or adjusted under 35 U.S.C. 154(b) by 15 days.

(21) Appl. No.: 11/904,968

(22) Filed: Sep. 27, 2007

(65) Prior Publication Data
US 2008/0095321 A1  Apr. 24, 2008

Related U.S. Application Data

(63) Continuation-in-part of application No. 11/453,451, filed on Jun. 14, 2006, now Pat. No. 7,290,928, which is a continuation of application No. 10/622,325, filed on Jul. 17, 2003, now Pat. No. 7,097,356.

(51) Int. Cl.
*A61B 6/14* (2006.01)
(52) U.S. Cl. .................. 378/170; 378/167; 378/168; 378/191
(58) Field of Classification Search ............... 378/168, 378/170, 191, 169
See application file for complete search history.

(56) References Cited

U.S. PATENT DOCUMENTS

| | | | |
|---|---|---|---|
| 4,554,676 A | | 11/1985 | Maldonado |
| 4,592,084 A | * | 5/1986 | McAuslan ............... 378/170 |
| 5,327,477 A | * | 7/1994 | Levy ........................ 378/168 |
| 6,033,111 A | * | 3/2000 | Winters et al. ............. 378/170 |
| 6,343,875 B1 | * | 2/2002 | Eppinger et al. ........... 378/170 |
| 6,592,256 B2 | * | 7/2003 | Da Rold et al. ............ 378/168 |
| 6,881,958 B2 | * | 4/2005 | Winters ..................... 250/353 |
| 6,905,244 B2 | * | 6/2005 | Kilcher et al. ............. 378/170 |
| 7,033,075 B2 | * | 4/2006 | Landis et al. ............... 378/168 |
| 7,195,395 B2 | * | 3/2007 | Quarry et al. .............. 378/170 |

FOREIGN PATENT DOCUMENTS

JP   2003-190150   7/2003

* cited by examiner

*Primary Examiner*—Allen C. Ho
(74) *Attorney, Agent, or Firm*—Gray Law Firm; Gordon E. Gray III

(57) ABSTRACT

The present invention is a radiographic sensor positioning system. In particular, the present invention is directed to a system for positioning a digital dental radiographic sensor in a patient's mouth and for positioning a radiographic device, e.g. a gamma ray source, to interact with the sensor. A preferred embodiment of the dental radiography positioning system comprises an aimer ring that slides onto an extension bar in one of several positions. The extension bar is preferably curved with a flared end and a tined end. The extension bar inserts into a bite block at one of three slots. The bite block has a bite surface above the three slots and a preferably tapered sensor holder slot with two stabilizer posts. A sensor holder is inserted into the sensor holder slot. For posterior images, the stabilizer posts can stabilize the sensor.

11 Claims, 11 Drawing Sheets

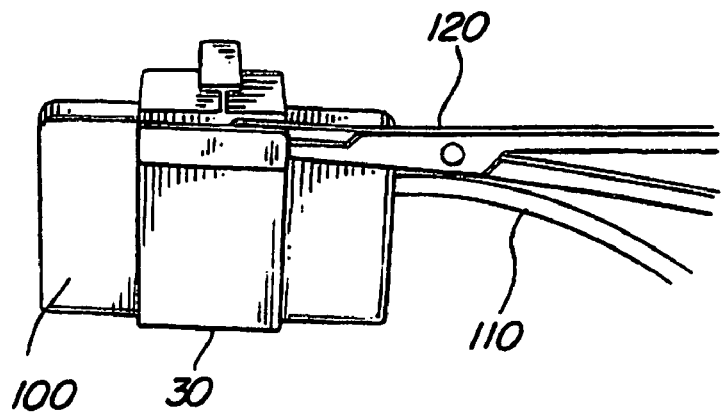
Fig. 3a
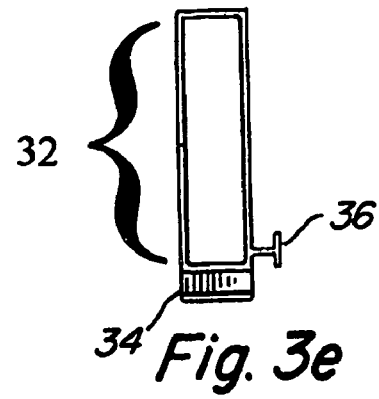
Fig. 3e
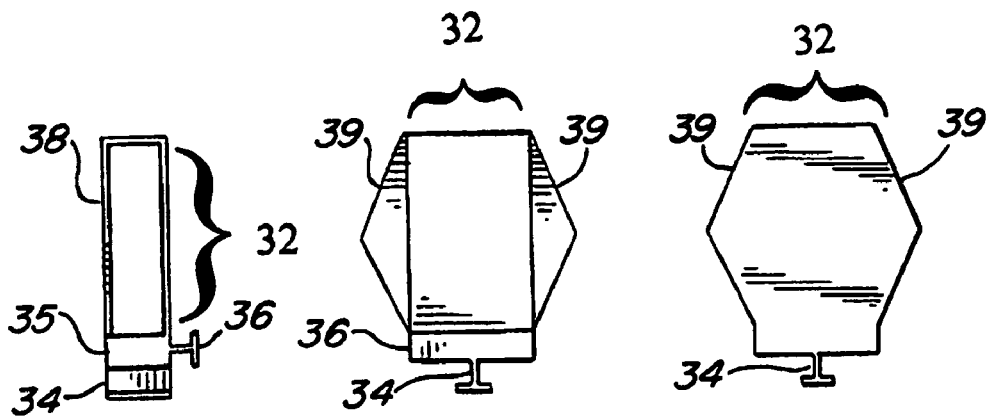
Fig. 3b  Fig. 3c  Fig. 3d

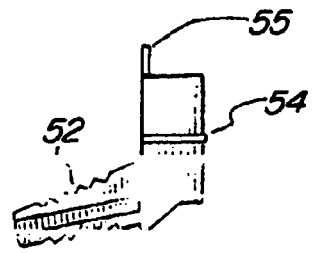
FIG. 8a
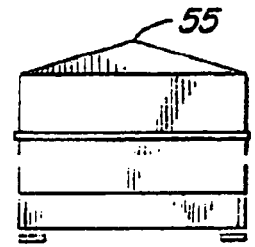
FIG. 8b
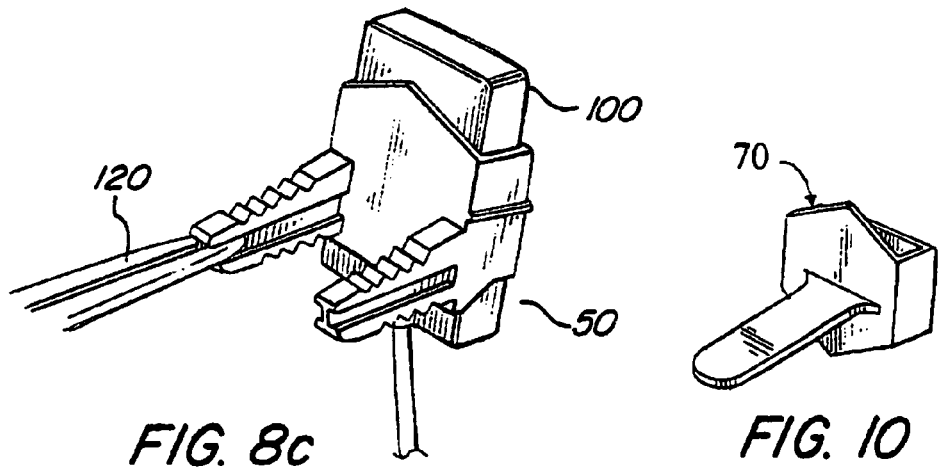
FIG. 8c
FIG. 10
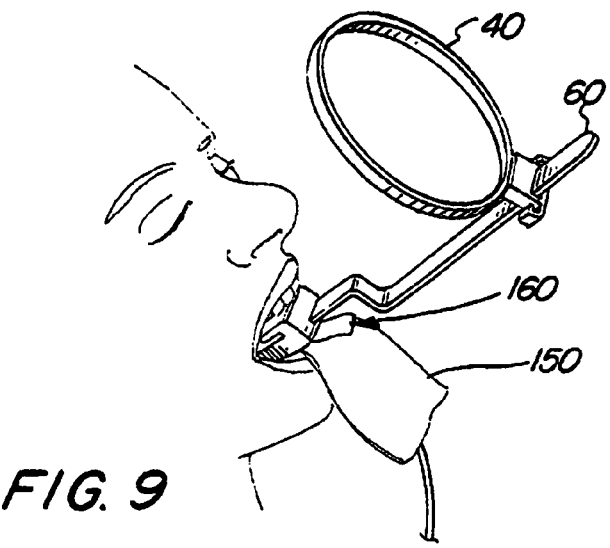
FIG. 9

RADIOGRAPHIC SENSOR POSITIONING SYSTEM

This is a continuation-in-part application of Ser. No. 11/453,451 filed on Jun. 14, 2006 now U.S. Pat. No. 7,290,928 that is a continuation of Ser. No. 10/622,325 now U.S. Pat. No. 7,097,356, filed Jul. 17, 2003. Said patent applications are incorporated herein by reference in their entirety.

TECHNICAL FIELD

The present invention is an improved radiographic sensor positioning system. In particular, the present invention is directed to a system for positioning a digital dental radiographic sensor in a patient's mouth and for positioning a radiographic device to interact with the sensor.

BACKGROUND ART

Several dental radiographic systems are known including U.S. Pat. Nos. 6,540,399, 6,203,195, 6,527,422, 6,461,038, 6,343,875, 6,203,195, 6,102,566, 5,677,537, and 5,652,779. Digital dental radiography is a relatively new procedure for examining a patient's teeth using significantly less radiation than traditional dental x-rays used to examine teeth. The procedure uses a sensor that is placed in the patient's mouth. Next, a source of gamma radiation is directed to the sensor. The sensor comprises pixels in an array that are influenced by the gamma radiation passing through the patient's teeth, and the pixels form an image which can be transmitted to a monitor for real-time viewing. One benefit of the procedure is that the amount of radiation needed to activate the sensor is far less than the amount of radiation that the patient is exposed to during x-ray procedures. Another benefit is the evaluation of real-time images allowing the dentist to reposition the sensor or acquire more images if needed without the delay associated with developing x-ray images on film. The images generally have a higher resolution than x-rays and can be manipulated using software to zoom and contrast and make more precise diagnostics.

SUMMARY OF THE INVENTION

The present invention is a radiographic sensor positioning system. In particular, the present invention is directed to a system for positioning a digital dental radiographic sensor in a patient's mouth and for positioning a radiographic device, e.g. a gamma ray source, to interact with the sensor. A preferred embodiment of the dental radiography positioning system comprises an aimer ring that slides onto an extension bar in one of several positions. The extension bar is preferably curved with a flared end and a tined end. The extension bar inserts into a bite block at one of three slots. The bite block has a bite surface above the three slots and a preferably tapered sensor holder slot with two stabilizer posts. A sensor holder is inserted into the sensor holder slot. For posterior images, the stabilizer posts can stabilize the sensor.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 3a is a side view of a preferred embodiment of the posterior sensor holder holding a sensor and being held by a hemostat;

FIG. 3b is an end view of a preferred embodiment of the posterior sensor holder;

FIG. 3c is a side view of a preferred embodiment of the posterior sensor holder;

FIG. 3d is a side view of a preferred embodiment of the posterior sensor holder;

FIG. 3e is a side view of a preferred embodiment of the posterior sensor holder for the #2 digital dental sensor;

FIG. 8a is a side view of a preferred embodiment of the anterior sensor holder;

FIG. 8b is a rear view of a preferred embodiment of the anterior sensor holder;

FIG. 8c is a perspective view of a preferred embodiment of the anterior sensor holder holding a digital dental sensor and being held by a hemostat;

FIG. 9 is a perspective view of a preferred embodiment of the invention inserted into a patient's mouth to obtain an anterior dental image;

FIG. 10 is a perspective view of a preferred embodiment of a vertical bitewing;

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an improved radiography positioning system.

Figure 1:
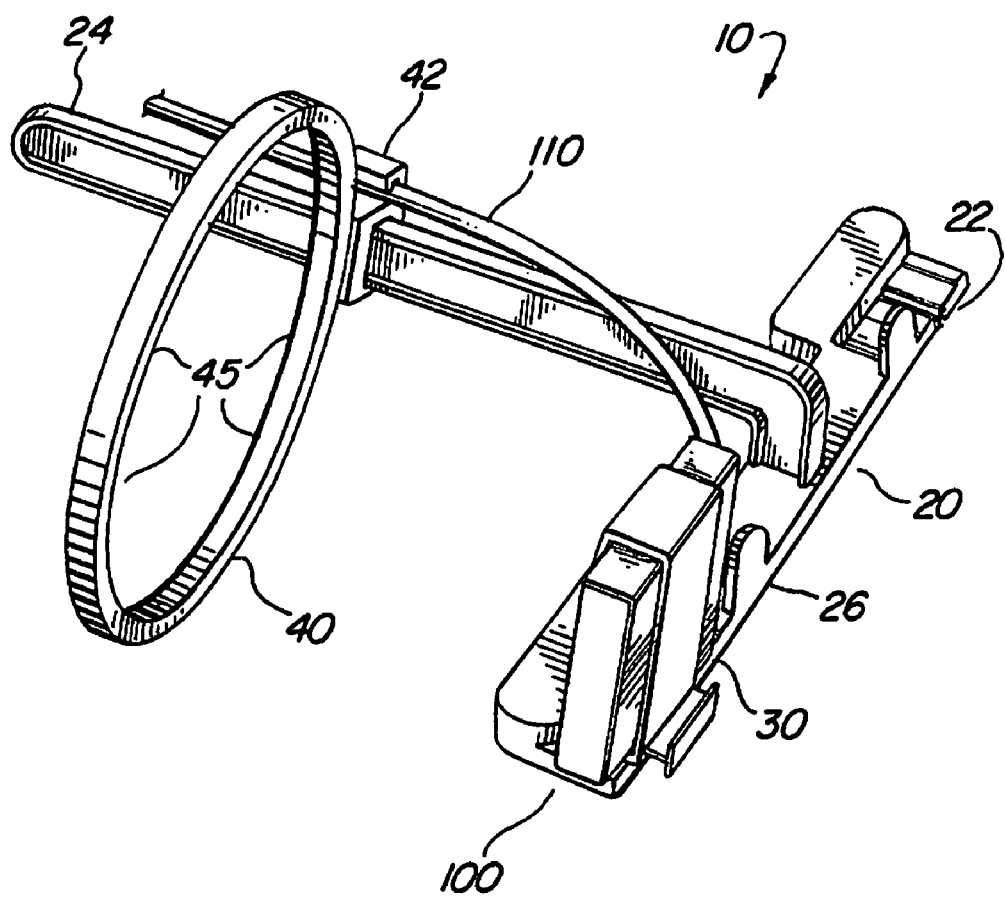
FIG. 1 is a perspective view of a preferred embodiment of the invention holding a digital dental sensor as used for obtaining posterior dental images.

Referring now to FIG. 1, a preferred embodiment of the invention 10 for taking posterior dental images is shown. As shown, the invention 10 holds a digital dental sensor 100 in a posterior sensor holder 30. The posterior sensor holder 30 is attached to a posterior imaging bar 20 at a slot 22. The posterior imaging bar 20 preferably has a T-like shape. One leg of the T-like shape is an aimer ring bar 24. The other leg of the T-like shape is an imaging bar 26. The invention 10 as shown in FIG. 1 is preferably configured to obtain an "Upper Left" posterior dental image when inserted in a patient's mouth.

As shown in FIG. 1, an aimer ring 40 slides onto the aimer ring bar 24. The aimer ring 40 is generally used to aim a radiography source (not shown) at the digital dental sensor 100. The aimer ring 40 preferably has a pair of hooks 42 to hold any wires 110 extending from the digital dental sensor 100. The aimer ring 40 is preferably configured such that when it is positioned on the aimer ring bar 24, the digital dental sensor 100 is visible within an interior view 45 of the ring 40. Preferably, to center the sensor holder 30 within the view 45 of the ring 40, the distance from center of the aimer ring 40 to the aimer ring bar 24 should be 1.75 inches. The ring 40 is generally mounted 9/16 inches above the aimer ring bar 24 and the aimer ring 40 is 3 inches in diameter.

Figure 2A:
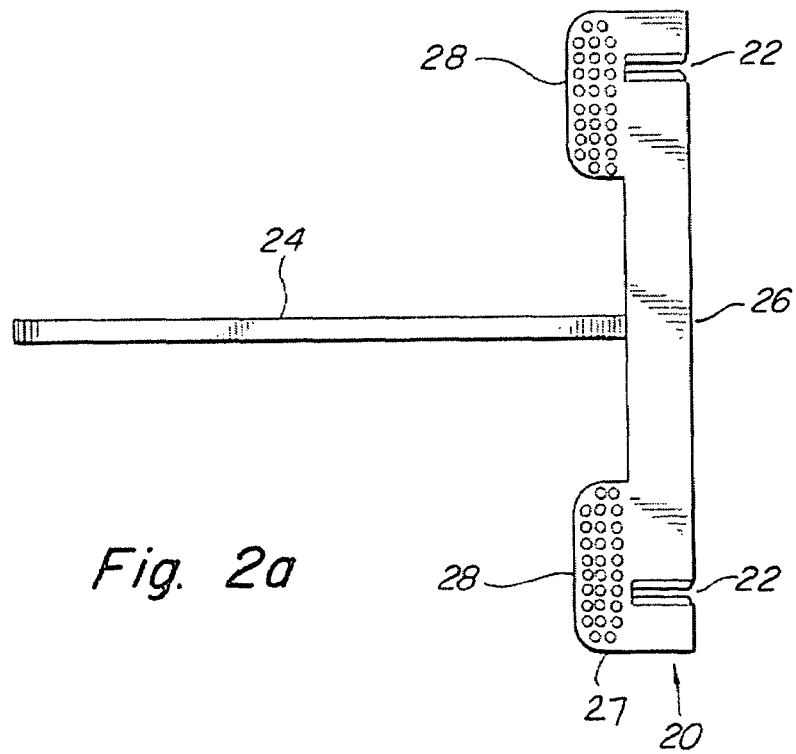
FIG. 2a is a bottom view of a preferred embodiment of the posterior imaging bar.

Referring now to FIG. 2a, a bottom view of a preferred embodiment of the posterior imaging bar 20 is shown. As is shown, the posterior imaging bar 20 is preferably T-shaped with opposing imaging platforms 28 with slots 22 and bite surfaces 27. Preferably, each side of the posterior imaging bar 20 is marked with the preferred dental image for which that side of the posterior imaging bar 20 is used. For example, in FIG. 2a, the bottom side of the posterior imaging bar is preferably used to obtain "lower right" and "lower left" posterior dental images. Thus, one side is marked "LR" and the other side is marked "LL."

The slots 22 can support a posterior sensor holder 30. Preferably, the slots have a radius-ed interior 23 as shown (and as shown in FIG. 2c). This tapered interior 23 allows the slot 22 to better support the posterior sensor holder 30. In particular, the radius-ed interior 23 is preferably used to grasp a sensor holder 30 with a sleeve base tab 34 that has an I-shaped cross-section.

Preferably, the posterior imaging bar has indentations 25 surrounding the slots 22 as shown in FIG. 2c. These indentations 25 provide lateral support to the posterior sensor holder 30 when it is inserted into one of the slots 22.

Figure 2B:
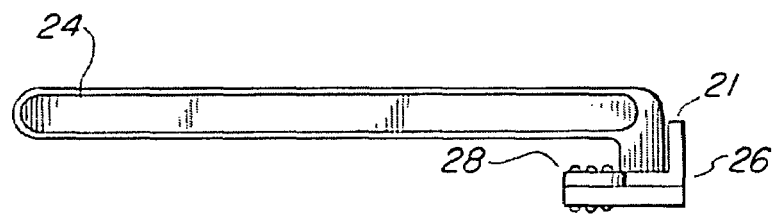
FIG. 2b is a side view of a preferred embodiment of the posterior imaging bar.
Figure 2C:
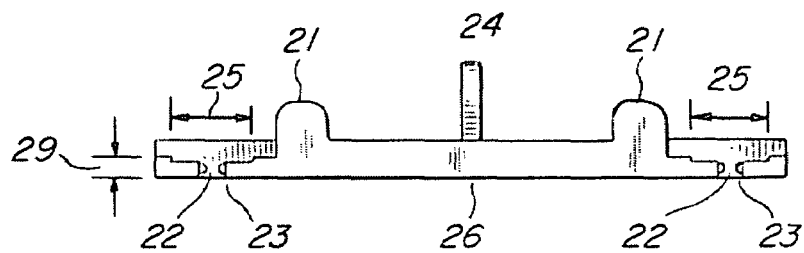
FIG. 2c is a front view of a preferred embodiment of the posterior imaging bar.

Referring to FIG. 2b, the aimer ring bar 24 is preferably set above the imaging bar 26 by a pre-determined distance. This distance is approximately ½ inch on center from the imaging bar 26 to the center of the aimer ring bar 24. Referring to FIG. 2c, the draft angle thickness 29 of the imaging bar 26 from the distal ends of the bar where the slots 22 are located increases as it proceeds to the center of the bar 26 where it connects to the aimer ring bar 24. This increase in thickness creates a preferable draft angle of 1.72 degrees (1.72°). This draft angle generally corresponds to the pan shape of a patient's mouth.

The imaging bar 26 preferably further comprises a pair of raised sensor supports 21 to prevent unwanted movement of the sensor 100 while the sensor 100 is inserted into the posterior sensor holder 30. The raised sensor supports 21, visible in FIG. 2c, help prevent elongated images and/or missed incisal edges that can occur if the sensor holder 30 is moved or folds over.

Referring now to FIG. 3a, a preferred embodiment of the posterior sensor holder 30 holding a sensor 100 is shown as held by a hemostat 120. As shown, a preferred embodiment of the posterior sensor holder 30 can be used with a hemostat 120 in addition to the posterior imaging bar 20. The posterior sensor holder 30 is preferably a sleeve 32 with a base and a back 38. The sleeve preferably has a sleeve base tab 34 for attachment to the posterior imaging bar 20 at the slots 22 and a gripping tab 36 for use with a gripping tool such as a hemostat 120.

Referring now to FIG. 3b, the sensor holder sleeve 32 is preferably flexible so that a variety of different digital dental sensors can be inserted in the holder 30. Preferably, the sensor holder sleeve 32 can deform in width 0.30 to 0.75 inches to accommodate a variety of sensors. Additionally, the sleeve back has triangular wings 39. The triangular wings 39 provide increased support for the digital dental sensor 100 to avoid unwanted movement when obtaining an image.

It should be noted that, in general, there are two sizes of digital dental sensors. The two sizes being most often referred to as either a #1 or #2 sensor; the #1 sensor being smaller than the #2 sensor. Accordingly, there are preferably two sizes of posterior sensor holder 30. The posterior sensor holder 30 for use with the #1 sensor is shown in FIGS. 3b-3d. The main difference between the posterior sensor holder for the #1 sensor and the #2 sensor is that the posterior sensor holder for the #1 sensor has a platform 35 at the base of the sleeve 32. This platform 35 is preferably 0.155 inches in thickness and is used to elevate the #1 sensor so that it is centered in the interior view of the aimer ring. The platform 35 is omitted from the base of the sleeve 32 in the posterior sensor holder for the #2 sensor as shown in FIG. 3e. The two different posterior sensor holders 30 allow the use of a single aimer ring with the system.

Figure 5:
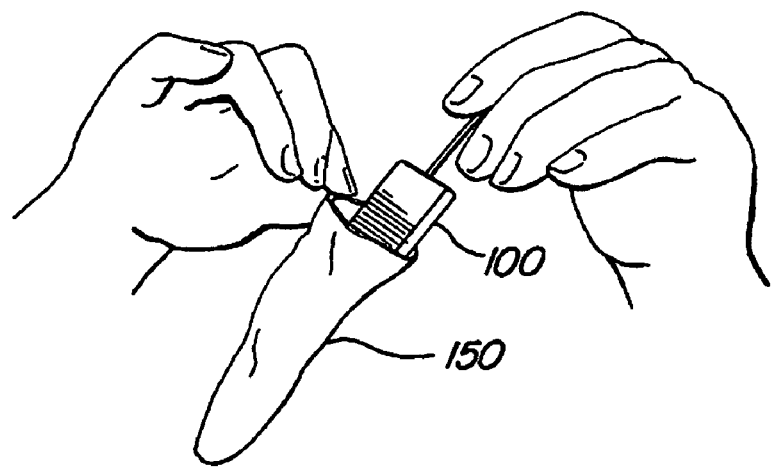
FIG. 5 is a perspective view of a sensor barrier being applied to a digital dental sensor.
Figure 4:
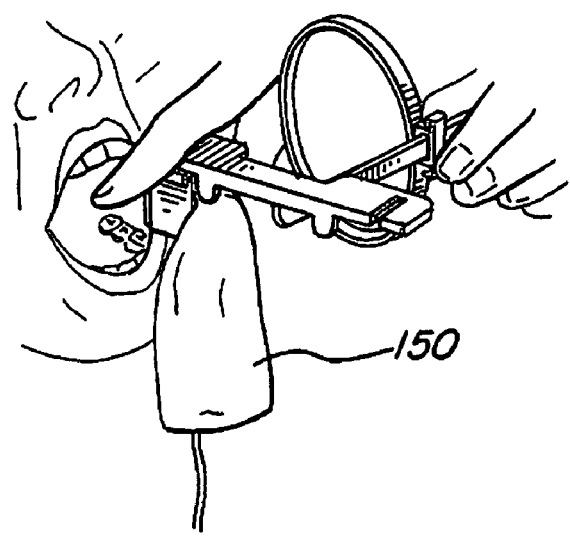
FIG. 4 is a perspective view of a preferred embodiment of the invention being inserted into a patient's mouth to obtain a posterior dental image.

FIG. 4 shows a preferred embodiment of the system in use. In particular, the invention is being used to take a lower left posterior dental image. The sensor holder 30 has been inserted into the proper slot 22 on the imaging bar 26 of the posterior imaging bar 20 to take a lower left posterior dental image. A digital dental sensor 100 has been inserted into a sensor barrier 150 (as shown in FIG. 5.)

This barrier 150 is used to reduce the need to sterilize the sensor 100 in between uses and patients. Instead, the barrier 150 is removed and discarded and a new barrier 150 applied.

The sensor 100, after being inserted in the barrier 150, is inserted into the posterior sensor holder 30. The barrier 150 provides the additional advantage of providing a more snug fit within the posterior sensor holder 30 (and, alternately, within the anterior sensor holder 50 as well). The posterior imaging bar 20, sensor holder 30, and sensor 100 with barrier 150 are inserted into the patient's mouth for the desired dental image. The patient then bites down on the bite surface 23 by the inserted sensor holder 30. As shown in FIG. 4, this positions the sensor 100 for an upper left posterior dental image. The radiography source, typically a gamma source, is aimed through the aimer ring 40 towards the digital dental sensor 100 to obtain an image.

Figure 6:
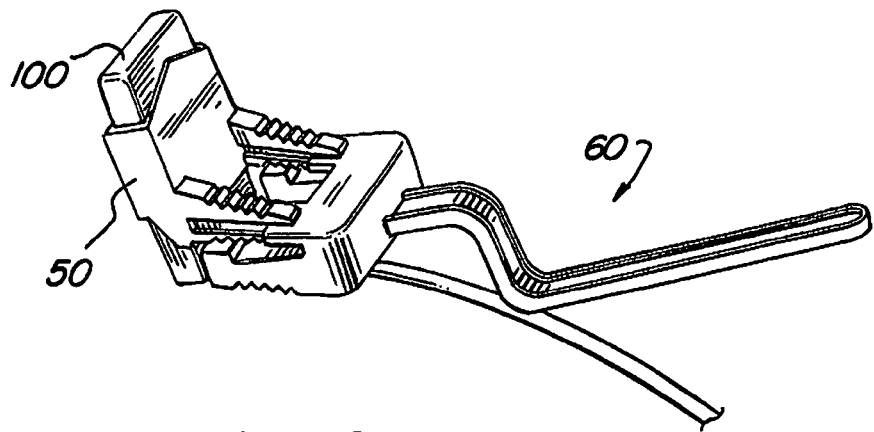
FIG. 6 is a perspective view of a preferred embodiment of the invention holding a digital dental sensor as used for obtaining anterior dental images.

Referring now to FIG. 6, a preferred embodiment of the system 10 as used for obtaining anterior dental images is shown. The digital dental sensor 100 is inserted in an anterior sensor holder 50. The anterior sensor holder 50 is held, in turn, by the anterior imaging bar 60.

Figure 7A:
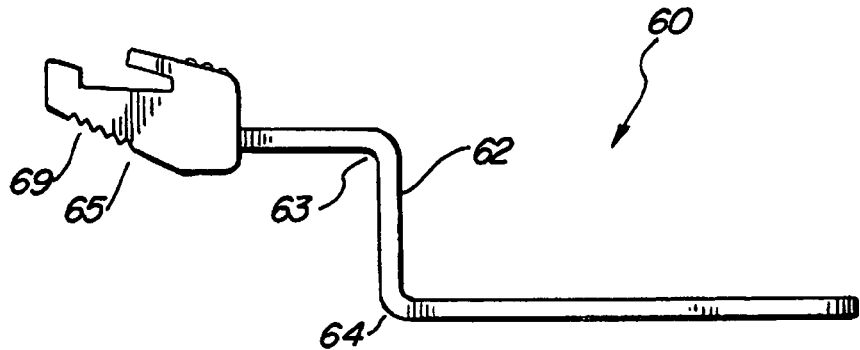
FIG. 7a is a side view of a preferred embodiment of the anterior imaging bar.

Referring now to FIG. 7a, a side view of a preferred embodiment of the anterior imaging bar 60 is shown. The anterior imaging bar 60 preferably comprises an anterior aimer ring bar 62. The anterior aimer ring bar 62 preferably has two approximately ninety degree (90°) bends 63, 64 and supports an anterior imaging platform 65. The anterior aimer ring bar 62 is shaped to hold the aimer ring 40 such that the anterior sensor holder 50 is held by the imaging bar 60 within the interior view of the aimer ring 40. With the sensor 100 held in this position, a practitioner easily captures acceptable images.

The positioning system in general reduces the occurrences of "cone cuts" and other undesired images. This reduces the number of image re-takes necessary, and thus, saves time and reduces the radiation exposure for the patient and dental staff.

Figure 7B:
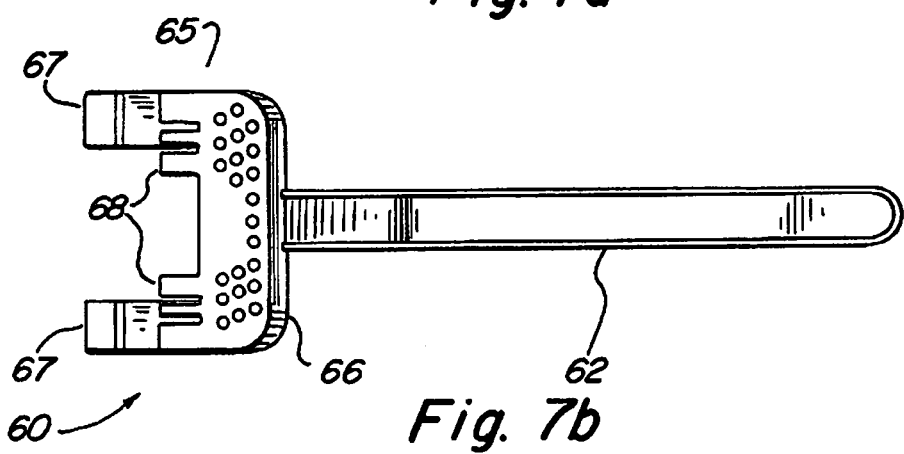
FIG. 7b is a top view of a preferred embodiment of the anterior imaging bar.

Referring now to FIG. 7b, a top view of a preferred embodiment of the anterior imaging bar 60 is shown. As shown, the anterior imaging platform 65 preferably comprises an anterior bite surface 66, two sets of pressure slots 68, and two sensor holder support arms 67. The sensor holder support arms 67 preferably extend from below the sets of pressure slots 68. The support arms 67 also preferably have a notched undersurface 69 to assist in holding the anterior imaging bar 60 in place in the patient's mouth while in use.

Referring now to FIG. 8a, a side view of a preferred embodiment of the anterior sensor holder 50 is shown. The anterior sensor holder 50 preferably has two sensor holder arms 52 that extend from a sleeve 54 downward and at an angle. The angle of the preferred embodiment between the sleeve 54 and the arms 52 is 114.12 degrees (114.12°). The angle can range from 100 to 115 degrees (100°-115°). As shown, the sensor holder arms 52 preferably have a rutted surface. This rutted surface provides patient's front (anterior) teeth a surface on which to bite and hold securely.

Referring to FIG. 8b, the sleeve 54 preferably has an extended angled peak 55. The angled peak 55 of the sleeve 54 provides additional support to the sensor 100 when held in the sleeve 54. Preferably, the system 10 has two anterior sensor holders 50 with differing widths to hold the #1 and #2 sizes of digital dental sensors 100.

Referring to FIG. 8c, a preferred embodiment of the anterior sensor holder 50 is shown with a digital dental sensor 100 in place and held by a hemostat 120. As shown, the sensor holder arms 52 preferably have an I-shaped cross-section. This cross-section allows the anterior sensor holder 50 to be held more easily by a gripping tool such as the hemostat 120 and provides for insertion and support by the set of pressure slots 68 on the anterior imaging bar 60. The sets of pressure slots 68 accommodate anterior sensor holders 50 with differing widths used to hold the #1 and #2 sizes of digital dental sensors 100.

FIG. 9 shows a preferred embodiment of the system positioned to acquire an anterior dental image from a patient. It should be noted that a cotton roll 160 could be inserted below the anterior imaging platform 65 to assist in positioning the system for imaging.

The preferred embodiment of the system 10 also includes a horizontal bitewing. The preferred horizontal bitewing is described in U.S. Pat. No. 6,520,676 that is incorporated herein by reference in its entirety. Thus, the system can position a digital dental sensor to acquire anterior, posterior and horizontal bitewing images.

The preferred embodiment of the system 10 also includes a vertical bitewing 70 as shown in FIG. 10. The vertical bitewing is used for vertical bitewing images. The preferred dimensions for the vertical bitewing 70 are made of similar material and similar in dimension to the horizontal bitewing described in U.S. Pat. No. 6,520,676 with the exception of the bitewing tab. The large bitewing sleeve is preferably 1.25"×10⁄32"×5⁄8" for the #1 sensor and the smaller bitewing sleeve is 1"×0.25"× 0.50" for the #2 sensor. This does not include the triangular wings extended from the sleeves. The large bitewing tab is preferably 1 5⁄8" long×1⁄2" wide×1⁄16" and the small bitewing tab is preferably 1 1⁄8" long×1⁄2" wide×1⁄16".

The posterior imaging bar 20 and the anterior imaging bar 60 are preferably made of material that can be hot (e.g. autoclaveable) or cold sterilized. Preferably, the bars 20, 60 are made of thermoplastic capable of withstanding temperatures of 220° F. for one hour without degradation such as high heat resistant grade polypropylene copolymer. The material should be capable of being hot and/or cold sterilization. The sensor holders 30 and 50 are preferably made of a material capable of only a single use. The material used for the sensor holders 30, 50 should show bite marks or discoloration or some other indicia that discourages re-use of the holders 30, 50 after a single use. Preferred materials for sensor holders 30, 50 include polyethylene, polypropylene, polyurethane, and nylon. Preferred melt flow ranges for these materials can be found in U.S. Pat. No. 6,520,676 incorporated herein by reference.

ALTERNATE PREFERRED EMBODIMENT OF SENSOR POSITIONING POSITION

Figure 11:
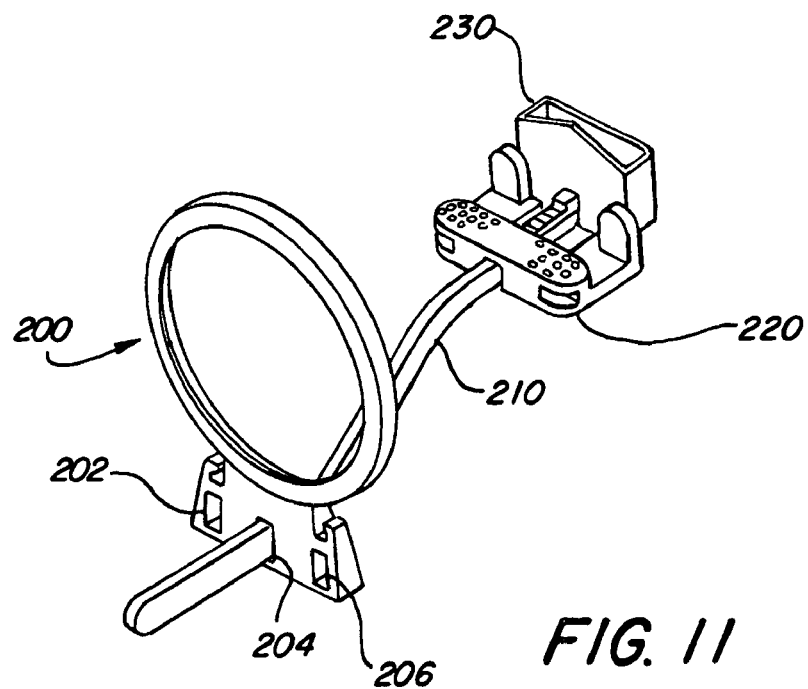
FIG. 11 is a perspective view of an alternate preferred embodiment configured for anterior imaging.

Another preferred embodiment of the radiographic sensor positioning system is herein described. The system can be used for anterior and posterior imaging. Referring now to FIG. 11, an alternate preferred embodiment of a radiographic sensor positioning system is shown configured for anterior imaging. An aimer ring 200 preferably has three main slots 202, 204, and 206 along its base. An imaging or extension bar 210 is preferably inserted into one of the main slots 202, 204, and 206. In FIG. 11, the extension bar 210 is inserted into the central main slot 204 to position the system for an anterior image.

Figure 12:
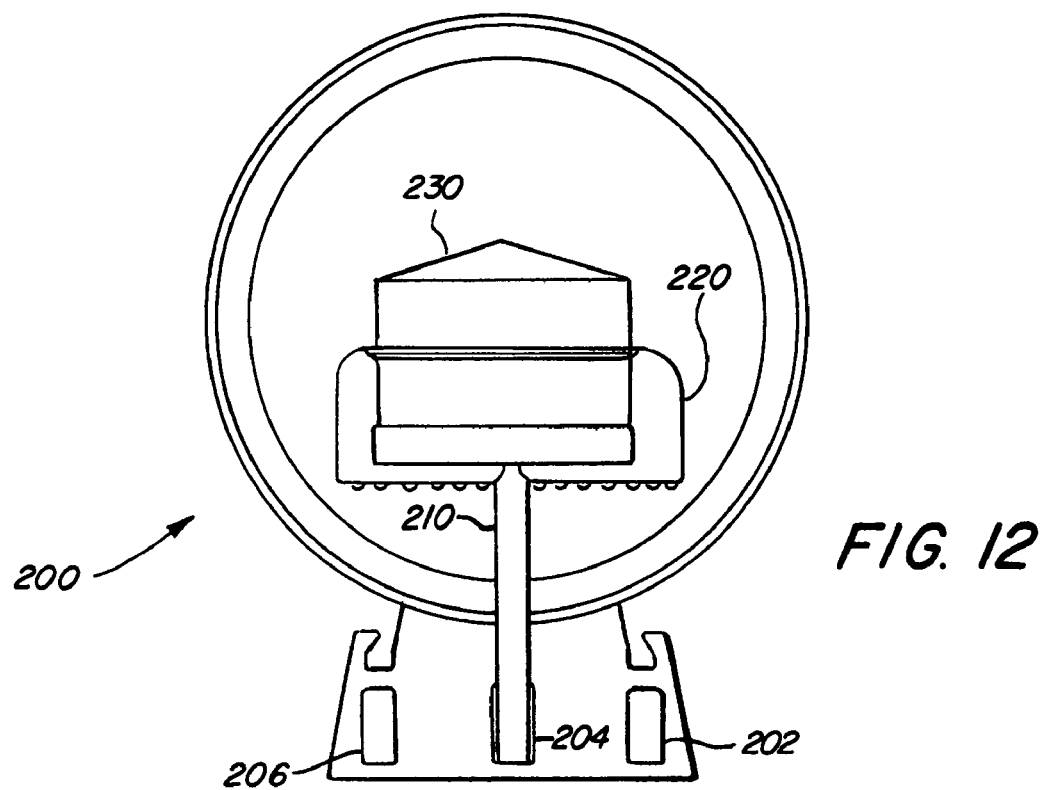
FIG. 12 is a rear view of the alternate preferred embodiment in FIG. 11.

The extension bar 210 is shaped, preferably curved, such that one end can position a bite block 220 and anterior sensor holder 230 in view of the central portion of the aimer ring 200. Thus, a radiographic source can be aimed into the ring at a sensor held by the system and centered radiographic images can be obtained. This is best shown in the rear view of the system configured for an anterior image in FIG. 12.

Figure 13:
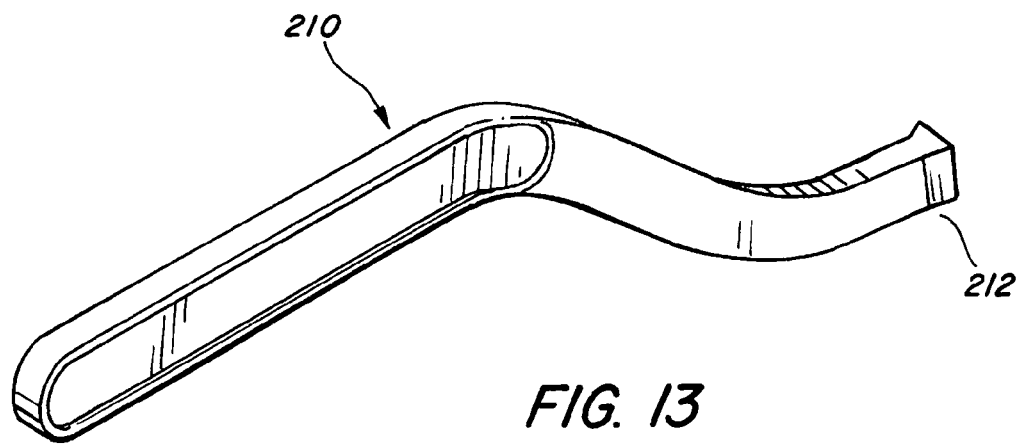
FIG. 13 is a perspective view of an alternate preferred embodiment of an imaging or extension bar.
Figure 15:
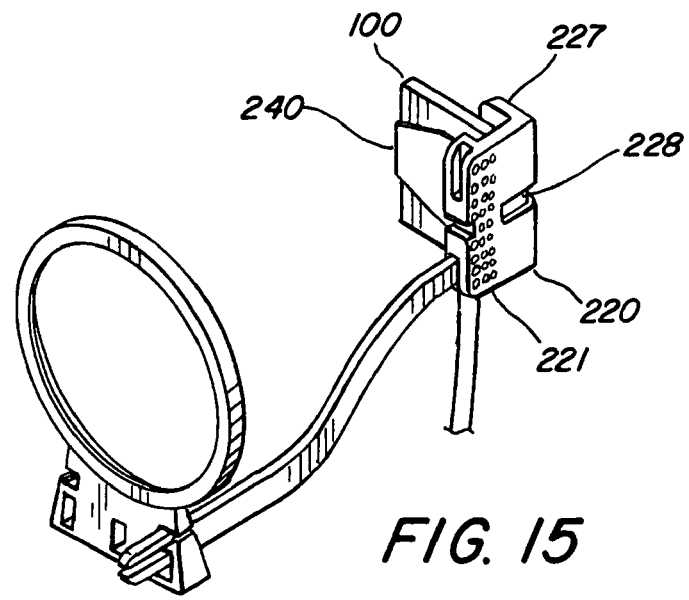
FIG. 15 is a perspective view of an alternate preferred embodiment configured for posterior imaging.
Figure 16:
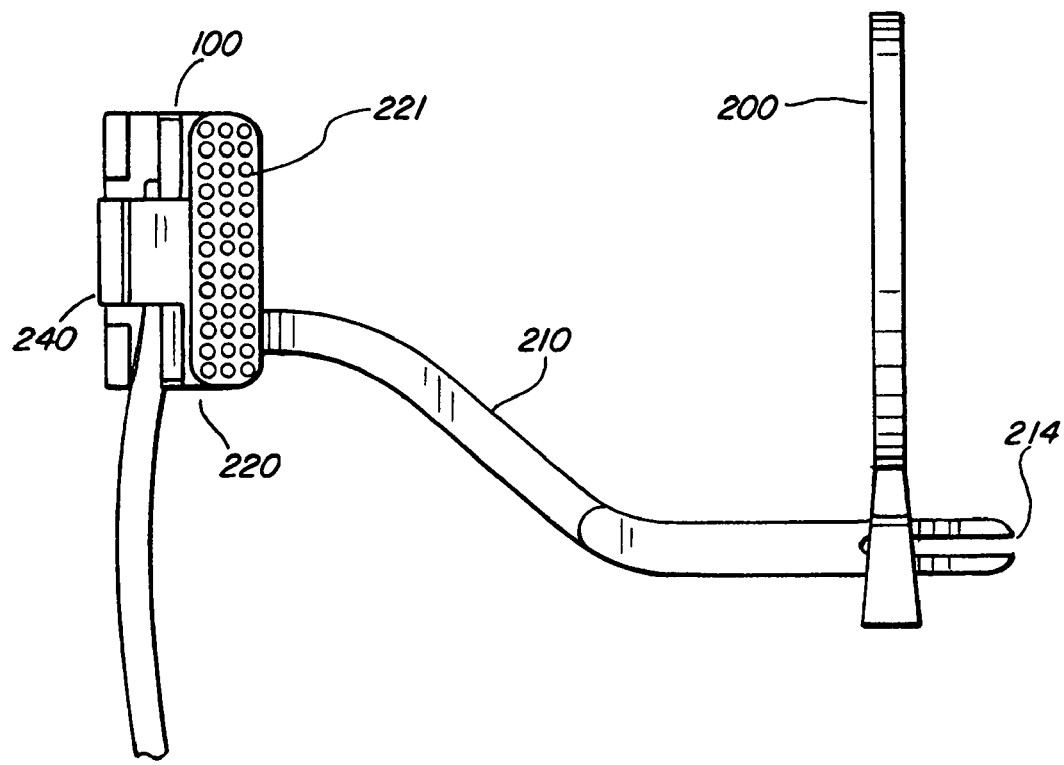
FIG. 16 is a side view of the alternate preferred embodiment shown in FIG. 15.

Referring now to FIG. 13, a perspective view of one of the preferred embodiments of the extension, or imaging, bar 210 is shown. As discussed, the extension bar 210 is preferably curved and has a flared end 212. The flared end 212 is inserted into slots on the bite block 220. The extension bar can also have a tined end 214 as shown in FIGS. 15 and 16 (discussed below.)

Figure 14:
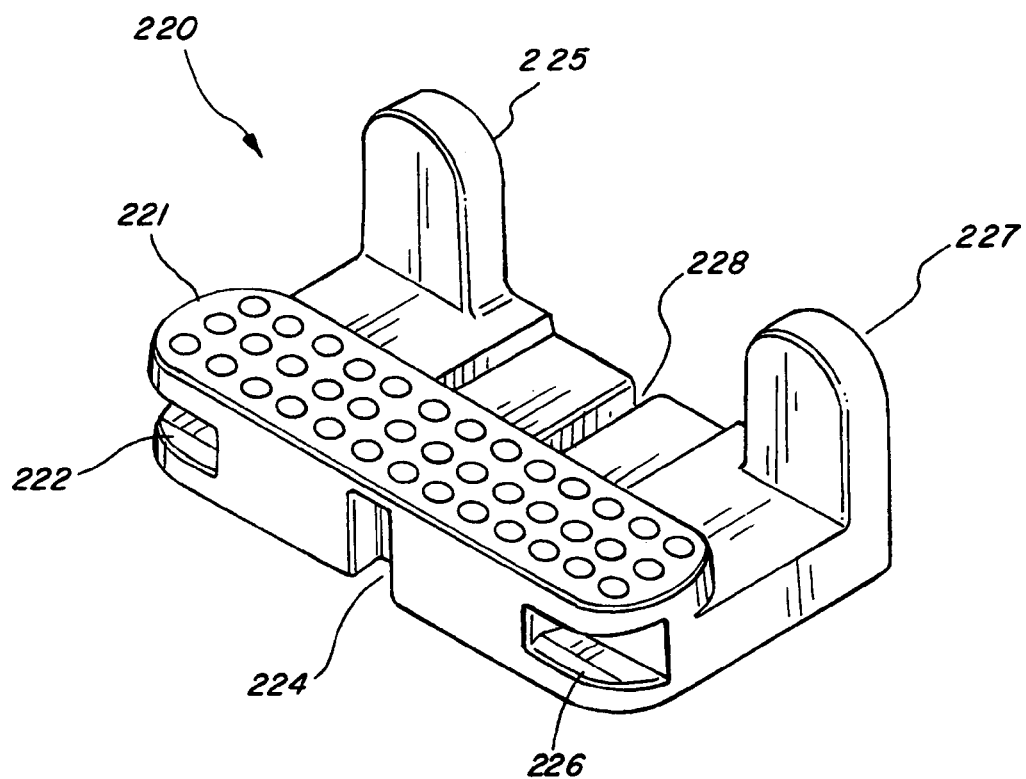
FIG. 14 is a perspective view of an alternate preferred embodiment of a bite block.

A preferred embodiment of the bite block 220 is shown in FIG. 14. The bite block 220 shown in FIG. 14 has a bite surface 221 and three slots 222, 224 and 226 for the extension bar 210. The flared end 212 of the extension bar assists in preventing the bar 210 from slipping out of the bite block 220. The two slots 222 and 226 are preferably used for posterior imaging. The slots 222 and 226 are preferably ½ inch in length (from flush outside to inside.) This allows the bar 210 to slide closer to the center of the bite block 220, which can relieve pressure on the bar 210 by the corner of a patient's cheek (retraction) and can prevent the bite block 220, sensor and posterior sensor holder 240 from moving upward in the patient's mouth. Thus, the system allows for complete apex to crown image capture of 3rd molars. The central slot 224 is preferably used for anterior imaging.

The bite block 220 preferably further comprises a sensor holder slot 228. The sensor holder slot 228 is preferably tapered to secure tabs extended from either a posterior sensor holder 240 or anterior sensor holder 230. As shown in FIG. 14, the bite block 220 also preferably has two stabilizer posts 225 and 227 spaced apart from the bite surface 221 and placed on either side of the sensor holder slot 228. As shown in FIG. 16, a posterior sensor holder 240 and a sensor 100 can be placed between the bite surface 221 and the stabilizer posts 225 and 227. Thus, the sensor 100 can be stabilized by the posts 225 and 227 as it is positioned in a patient's mouth.

Figure 17:
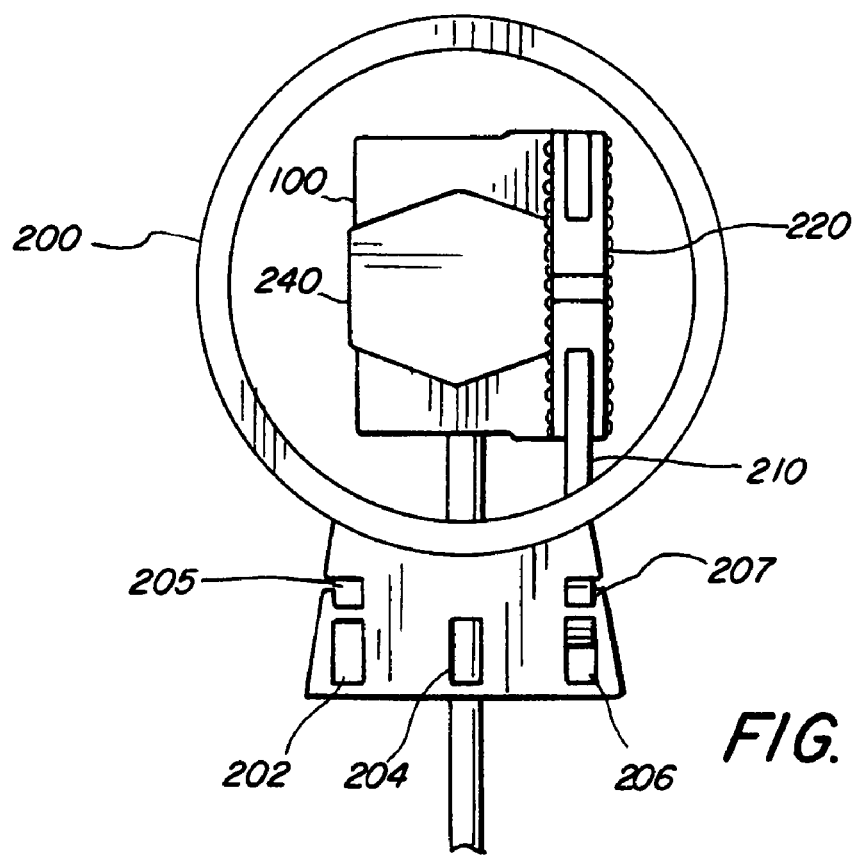
FIG. 17 is a front view of the alternate preferred embodiment shown in FIG. 15.
Figure 20:
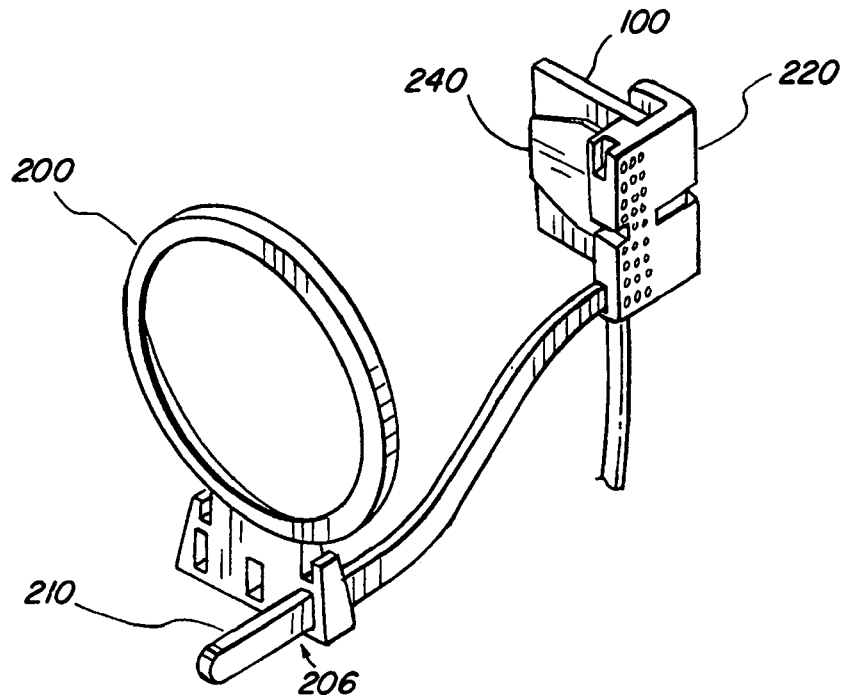

Referring again to FIG. 15, a perspective view of an alternate preferred embodiment of the system configured for posterior imaging is shown. The flared end 212 of the extension bar 210 is inserted into the slot 222 on the bite block 220. The posterior sensor holder 240 is inserted into the sensor holder slot 228 on the bite block 220 and positioned between the stabilized posts 225 and 227 and the bite surface 221. The aimer ring 200 is placed onto the tined end 214 of the extension bar 210. As discussed above, the aimer ring 200 has three main, or major, slots 202, 204 and 206. Preferably, the aimer ring 200 also has two minor slots 205 and 207. The minor slots 205 and 207 allow one tine of the tined end 214 of the extension bar to be inserted into at least two more positions on the aimer ring 200. As shown in FIG. 17, the one tine of the tined end 214 has been inserted into the minor slot 207 and one tine of the tined end 214 has been inserted into the major slot 206. This configuration provides a slightly higher positioning of the sensor 100 inside the aimer ring 200 for extreme posterior (third molar) images and provides more comfort for the patient. A posterior configuration with the extension bar 210 in the lower position, e.g. solely in major slot 206, is shown in FIG. 20. (The configuration in FIG. 20 does not require, but can be set up with, an extension bar 210 with a tined end 214.)

Figure 18:
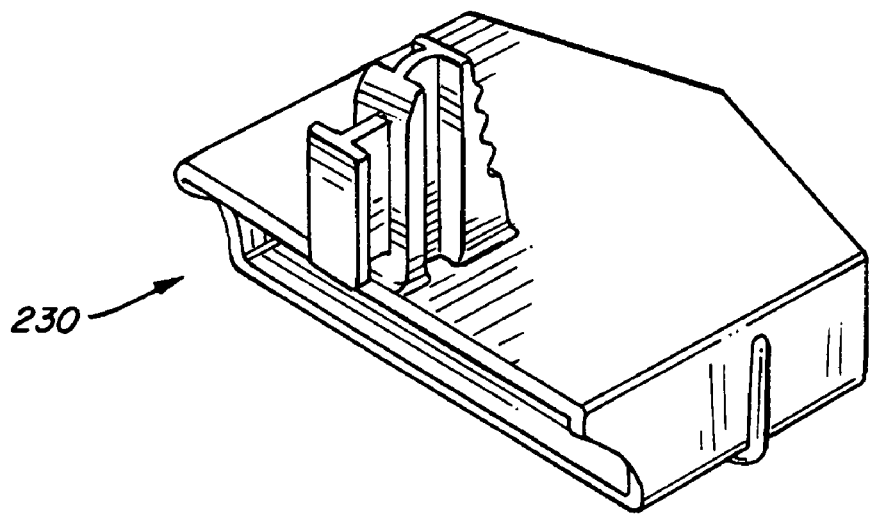
FIG. 18 is a perspective view of an alternate preferred embodiment of an anterior sensor holder.
Figure 19:
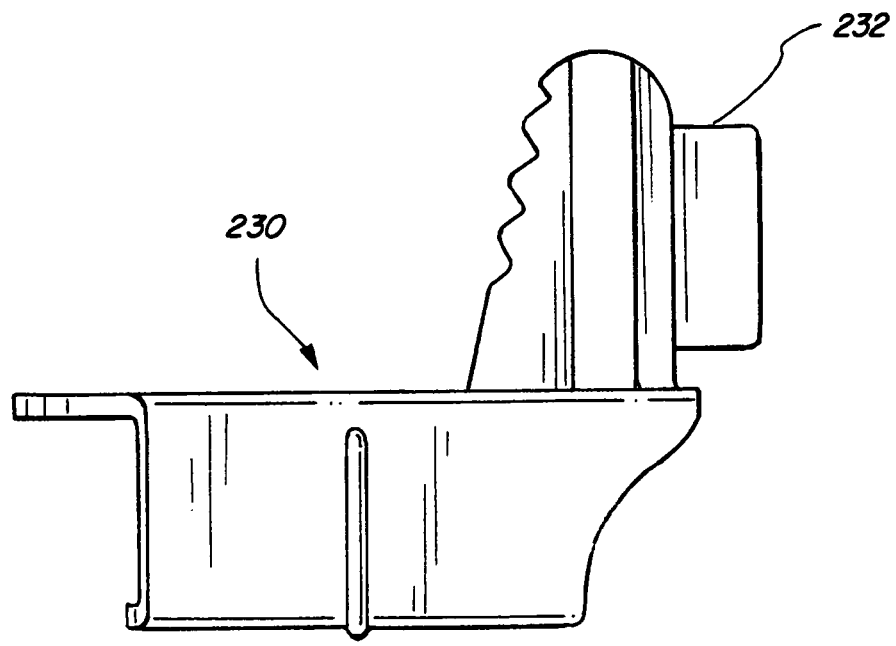
FIG. 19 is a side view of the alternate preferred embodiment of the anterior sensor holder in FIG. 18; and, FIG. 20 is a perspective view of an alternate preferred embodiment configured for posterior imaging with an extension bar inserted into a major slot on an aimer ring.

The embodiments of the posterior sensor holder shown in FIGS. 3a-3d are useable with the present alternate embodiment. However, it is preferable that a single arm anterior sensor holder 230 be used with the present alternate embodiment. The preferred embodiment of the single arm anterior sensor holder 230 is shown in FIGS. 18 and 19. As shown in FIGS. 18 and 19, the anterior sensor holder 230 has a single arm 232 in contrast to FIGS. 8a-8c. However, the single arm 232 still preferably has a tab with an I-shaped cross-section for insertion into the sensor holder slot 228 on the bite block 220.

Thus, an improved radiographic sensor positioning system is described above that is capable of positioning a digital dental sensor for anterior and posterior dental images. The preferred alternate embodiment uses only a single extension bar, aimer ring and a more compact bite block. It also provides for multiple imaging configurations and for even extreme imaging like a third molar image. In each of the above embodiments, the different positions and structures of the present invention are described separately in each of the embodiments. However, it is the full intention of the inventor of the present invention that the separate aspects of each embodiment described herein may be combined with the other embodiments described herein. Those skilled in the art will appreciate that adaptations and modifications of the just-described preferred embodiment can be configured without departing from the scope and spirit of the invention. For example, the system's sensor holders could be re-configured to hold dental x-ray film for more traditional dental imaging. Therefore, it is to be understood that, within the scope of the appended claims, the invention may be practiced other than as specifically described herein.

What is claimed is:

1. A dental radiographic sensor positioning system comprising:
   an extension bar;
   an aimer ring having a ring and a slotted base that slidingly engages the extension bar;
   a bite block having a bite surface, a posterior imaging slot and an anterior imaging slot where the posterior imaging slot and the anterior imaging slot alternately engage the extension bar, and a sensor holder slot; and,
   a sensor holder.

2. The dental radiographic sensor positioning system of claim 1 where the extension bar has a tined end that inserts in the slotted base of the aimer ring.

3. The dental radiographic sensor positioning system of claim 2 where the slotted base of the aimer ring has three slots, where the three slots provide at least five different positions for the extension bar.

4. The dental radiographic sensor positioning system of claim 1 where the extension bar has a flared end that inserts into the anterior imaging slot or the posterior imaging slot on the bite block.

5. The dental radiographic sensor positioning system of claim 1 where the bite block has two stabilizer posts.

6. A dental radiographic sensor positioning system comprising:
   an extension bar;
   an aimer ring having a ring and a base with three major slots that alternately and slidingly engage the extension bar at a tined end of the extension bar; the extension bar further having a flared end;
   a bite block having a bite surface, two posterior imaging slots, an anterior imaging slot positioned between the two posterior imaging slots, and a tapered sensor slot between two stabilizer posts;
   a sensor holder having a tab that inserts into the tapered sensor slot.

7. The dental radiographic sensor positioning system of claim 6 where the three major slots are the first, second and third major slots;
   the base further comprises a first minor slot positioned over the first major slot and a second minor slot positioned over the third major slot;
   the tined end of the extension bar comprises a first and second tine; where the first tine inserts into the first minor slot and second tine inserts into the first major slot or the first tine inserts into the second minor slot and the second tine inserts into the third major slot.

8. A dental radiography bite block comprising:
   three slots;
   a bite surface above the three slots;
   a first stabilizer post and a second stabilizer post;
   a sensor holder slot, said sensor holder slot placed below and between the first and second stabilizer posts, and spaced apart from the three slots.

9. The dental radiography bite block of claim 8 where two of the three slots are for positioning an extension bar for posterior imaging and where at least one of the three slots is for positioning an extension bar for anterior imaging.

10. The dental radiography bite block of claim 8 where the sensor holder slot is tapered.

11. The dental radiography bite block of claim 8 where the first and second stabilizer posts are spaced sufficiently apart from the bite surface to allow insertion of a sensor holder and a sensor between the bite surface and the first and second stabilizer posts and to provide stability to the sensor.

* * * * *